US010488515B2

(12) United States Patent
Kawamura et al.

(10) Patent No.: US 10,488,515 B2
(45) Date of Patent: Nov. 26, 2019

(54) ACOUSTIC EMISSION WAVE DETECTION SYSTEM FOR A HIGH VOLTAGE APPARATUS

(71) Applicant: HITACHI, LTD., Chiyoda-ku, Tokyo (JP)

(72) Inventors: Daichi Kawamura, Tokyo (JP); Toru Masuda, Tokyo (JP); Hiroshi Kageyama, Tokyo (JP); Ayumu Hatanaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 243 days.

(21) Appl. No.: 15/529,427

(22) PCT Filed: Nov. 25, 2014

(86) PCT No.: PCT/JP2014/081116
§ 371 (c)(1),
(2) Date: May 24, 2017

(87) PCT Pub. No.: WO2016/084133
PCT Pub. Date: Jun. 2, 2016

(65) Prior Publication Data
US 2017/0329006 A1 Nov. 16, 2017

(51) Int. Cl.
G01S 15/89 (2006.01)
G01N 29/14 (2006.01)
(Continued)

(52) U.S. Cl.
CPC ......... *G01S 15/8968* (2013.01); *G01H 9/004* (2013.01); *G01N 21/6402* (2013.01);
(Continued)

(58) Field of Classification Search
CPC .............................. G01S 15/8968; G01H 9/004; G01N 21/6402; G01N 29/14; G01N 29/2418;
(Continued)

(56) References Cited

U.S. PATENT DOCUMENTS 6,984,819 B2 * 1/2006 Ogawa ................... G01H 9/004
250/227.21
8,820,167 B2 * 9/2014 Diatzikis ................ G01H 9/004
250/227.18
(Continued)

FOREIGN PATENT DOCUMENTS

JP   2002-90413 A    3/2002
JP   2003-169801 A   6/2003
(Continued)

OTHER PUBLICATIONS

International Search Report (PCT/ISA/210) issued in PCT Application No. PCT/JP2014/081116 dated Mar. 10, 2015 with English translation (five (5) pages).
(Continued)

*Primary Examiner* — Harshad R Patel
*Assistant Examiner* — Nigel H Plumb
(74) *Attorney, Agent, or Firm* — Crowell & Moring LLP

(57) ABSTRACT

An acoustic emission wave detection system and an acoustic emission wave detector are provided. The acoustic emission wave detection system includes an acoustic emission wave detector, a photoelectric converter, and a determination processor. The acoustic emission wave detector includes a housing, an optical fiber that guides light from a wideband light source into the housing, and an FBG housed in the housing and having a diffractive grating that reflects light guided into the housing. The FBG is fixed on a side of the other end in the housing such that the light guided into the housing is received by one end thereof. An acoustic emission wave from a high-voltage apparatus is received by the other end thereof. Due to the insulation resistance of the FBG, the acoustic wave detector can be installed close to or in contact with the high-voltage apparatus without introducing discharges or noise from the high-voltage apparatus.

15 Claims, 14 Drawing Sheets

(51) Int. Cl.
    *G01H 9/00*    (2006.01)
    *G01N 21/64*   (2006.01)
    *H04B 10/079*  (2013.01)
    *H04R 23/00*   (2006.01)
    *G01N 29/24*   (2006.01)
    *G01N 29/42*   (2006.01)

(52) U.S. Cl.
    CPC ......... *G01N 29/14* (2013.01); *G01N 29/2418* (2013.01); *G01N 29/42* (2013.01); *H04B 10/07957* (2013.01); *H04R 23/008* (2013.01)

(58) Field of Classification Search
    CPC .............. G01N 29/42; H04B 10/07957; H04R 23/008; G01J 1/34
    See application file for complete search history.

(56) References Cited

U.S. PATENT DOCUMENTS

2002/0166955 A1   11/2002   Ogawa
2003/0181802 A1*  9/2003   Ogawa ................... G01H 9/004
                                                      600/407
2012/0204651 A1*  8/2012   Diatzikis ................ G01H 9/004
                                                      73/655
2014/0114187 A1*  4/2014   Rozental ................ G01H 9/004
                                                      600/437

FOREIGN PATENT DOCUMENTS

| JP | 2003-337063 A | 11/2003 |
|---|---|---|
| JP | 2003-339707 A | 12/2003 |
| JP | 2006-84266 A | 3/2006 |
| JP | 2014-505887 A | 3/2014 |

OTHER PUBLICATIONS

Japanese-language Written Opinion (PCT/ISA/237) issued in PCT Application No. PCT/JP2014/081116 dated Mar. 10, 2015 (four (4) pages).

\* cited by examiner

ACOUSTIC EMISSION WAVE DETECTION SYSTEM FOR A HIGH VOLTAGE APPARATUS

TECHNICAL FIELD

The present invention relates to an acoustic emission wave detector and so on that detects acoustic emission waves.

BACKGROUND ART

When a defective portion such as a void, a crack or the like is present in an insulator (for example, an insulator used for wire coating) provided in a high-voltage apparatus, it is known that the electric field is concentrated in the defective portion during operation of the high-voltage apparatus and a feeble discharge called a partial discharge occurs.

If the operation of the high-voltage apparatus continues in a state in which a partial discharge has occurred, the void or crack develops and a dielectric breakdown occurs, which may lead to a failure of the high-voltage apparatus. Thus, before a dielectric breakdown occurs, detecting a partial discharge suitably as a sign phenomenon thereof is demanded.

As one detection technique of a partial discharge, the AE method that detects acoustic emission waves (hereinafter, called AE waves) can be cited. An AE wave is an elastic wave (acoustic wave) generated by energy stored in an insulator or the like. An AE wave is emitted from the defective portion when a partial discharge occurs and thus, a sign of the dielectric breakdown can be known by detecting the AE wave.

For example, PTL 1 describes an insulation failure diagnostic apparatus that diagnoses the presence/absence of a partial discharge (insulation failure) of a high-voltage apparatus based on the detection value of an AE sensor. The above AE sensor is installed in a housing in which the high-voltage apparatus is housed.

CITATION LIST

Patent Literature

PTL 1: JP 2002-90413 A

SUMMARY OF INVENTION

Technical Problem

As described above, the AE sensor described in PTL 1 is mounted on a housing that houses a high-voltage apparatus. That is, an AE wave is detected indirectly via the housing and thus, the AE wave may attenuate before reaching the AE sensor so that the AE wave may not be suitably detected.

Incidentally, mounting an AE sensor using the piezoelectric effect directly on the high-voltage apparatus can be considered. However, if the AE sensor is mounted on the high-voltage apparatus, an electromagnetic wave (noise) emitted from the high-voltage apparatus is superimposed on an electric signal of the AE sensor, which may invite deterioration of the detection precision of an AE wave. Also, the AE sensor may fail due to a discharge from the high-voltage apparatus.

Thus, a problem is posed that it is difficult to suitably detect an AE wave by an AE sensor using the piezoelectric effect.

An object of the present invention is to provide an acoustic emission wave detector and so on that suitably detects acoustic emission waves.

Solution to Problem

In order to solve the object, an acoustic emission wave detector according to the present invention includes: a housing; a first optical fiber that guides light from a light source into the housing; and a second optical fiber housed inside the housing and having a diffractive grating that reflects the light guided into the housing, wherein the second optical fiber is fixed in the housing on a side of the other end so as to receive the light guided into the housing by one end thereof and to receive an acoustic emission wave from an object by the other end.

Details thereof will be described in Description of Embodiments.

Advantageous Effects of Invention

According to the present invention, an acoustic emission wave detector and so on that suitably detects acoustic emission waves can be provided.

BRIEF DESCRIPTION OF DRAWINGS

FIG. 4A is an explanatory view when FBG is normal without expansion and contraction, FIG. 4B is an explanatory view when the period of the diffractive grating is shortened due to contraction of FBG, and FIG. 4C is an explanatory view when the period of the diffractive grating is prolonged due to expansion of FBG.

FIG. 6A is an explanatory view when FBG is without expansion and contraction, FIG. 6B is an explanatory view when the period of the diffractive grating is shortened due to contraction of FBG, and FIG. 6C is an explanatory view when the period of the diffractive grating is prolonged due to expansion of FBG.

DESCRIPTION OF EMBODIMENTS

Hereinafter, an acoustic emission wave detection system S1 (see FIG. 1) is denoted as an "AE wave detection system S1". Also, an acoustic emission wave detector 3 (see FIG. 1) is denoted as an "AE wave detector 3".

First Embodiment

<Configuration of the AE Wave Detection System>

Figure 1:
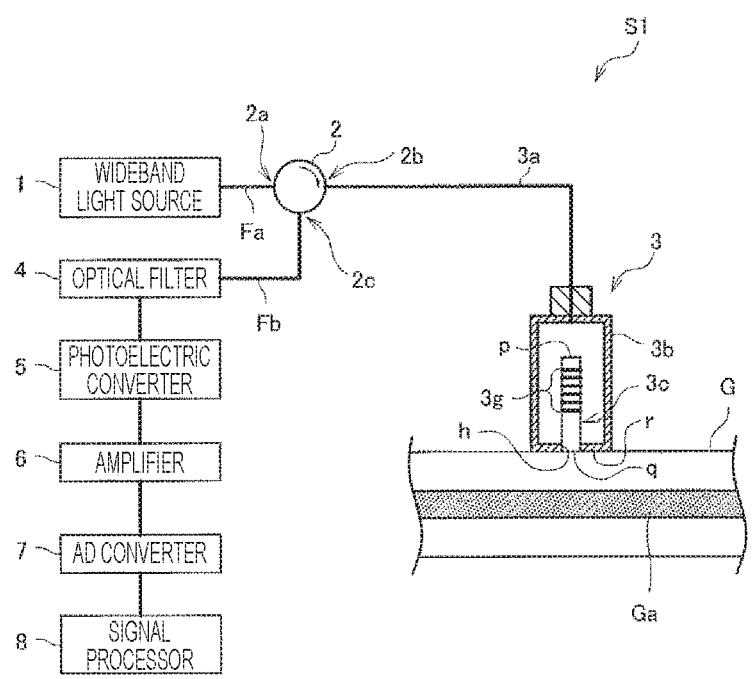
FIG. 1 is a schematic diagram of an acoustic emission wave detection system according to a first embodiment of the present invention.

FIG. 1 is a schematic diagram, of the AE wave detection system S1 according to the first embodiment. Regarding the AE wave detector 3, a vertical section thereof is illustrated. The AE wave detection system S1 is a system that detects an AE wave generated by a high-voltage apparatus G (object).

The high-voltage apparatus G shown in FIG. 1 is, for example, a high-voltage line. An insulator Ga provided in the high-voltage apparatus G is, for example, an insulator covering a conductor of the high-voltage line.

The AE wave detection system. S1 includes a wideband light source 1, an optical circulator 2, the AE wave detector 3, an optical filter 4, a photoelectric converter 5, an amplifier 6, an analog-digital (AD) converter 7, and a signal processor 8.

The wideband light source 1 (light source) is a light source that emits light in a relatively wide wavelength band. A lamp, a light emitting diode (LED) light source or the like can be used as the wideband light source 1. The light of the wideband light source 1 is emitted toward one end of an optical fiber Fa.

The optical circulator 2 (optical guideway forming device) is configured in such a way that light incident on a first port 2a from the wideband light source 1 via the optical fiber Fa propagates toward an optical fiber 3a. The optical circulator 2 is also configured in such a way that light incident on a second port 2b from a fiber Bragg grating (hereinafter, FBG) 3c described below via the optical fiber 3a propagates toward an optical fiber Fb.

The optical fiber Fa is connected to the first port 2a of the optical circulator 2, the optical fiber 3a is connected to the second port 2b, and the optical fiber Fb is connected to a third port 2c.

The AE wave detector 3 is used to detect (extract) an AE wave emitted by a partial discharge of the insulator Ga as a change of the wavelength of light. The AE wave detector 3 includes the optical fiber 3a, a housing 3b, and the FBG 3c.

The optical fiber 3a (first optical fiber) is an optical device that guides light from the wideband light source 1 into the housing 3b and also guides light reflected by the FBG 3c into the optical filter 4. The optical fiber 3a includes a core (not shown) having a relatively high refractive index, a clad (not shown) covering surroundings of the core and having a refractive index lower than that of the core, and a coating (not shown) covering surroundings of the clad to protect the core and the clad. Then, light is made to propagate inside the optical fiber 3a by repeating total reflection on the boundary surface between the core and the clad.

One end of the optical fiber 3a is fixed to the housing 3b while facing the inside of the housing 3b. The other end of the optical fiber 3a is connected to, as described above, the second port 2b of the optical circulator 2.

The housing 3b is a shell-shaped member housing the FBG 3c described below and also installed on the high-voltage apparatus G and has an installation surface r (In FIG. 1, an undersurface) installed on the high-voltage apparatus G. An insertion hole (not shown) to insert the optical fiber 3a is provided in a location where the optical fiber 3a is connected of a top wall of the housing 3b.

Also, a hole h where the FBG 3c is installed is provided in a bottom wall on the opposite side of the insertion hole (the side on which the housing 3b is installed on the high-voltage apparatus G) in the housing 3b.

As shown in FIG. 1, the housing 3b is mounted on the high-voltage apparatus G in a state in which a lower end q (the other end) of the FBG 3c is brought close to the high-voltage apparatus G. An adhesive such as silicone grease may be used to install the housing 3b on the high-voltage apparatus G or a magnet may be embedded in the bottom wall of the housing 3b in contact with the high-voltage apparatus G.

The FBG 3c (second optical fiber) is an optical fiber optical fiber having a diffractive grating 3g that reflects light guided into the housing 3b and is housed inside the housing 3b. As shown in FIG. 1, the FBG 3c is fixed inside the housing 3b in such a way that the lower end q (the other end) is directed to the high-voltage apparatus G and the upper end (one end) is directed to the opposite direction of the high-voltage apparatus G when the AE wave is detected.

Figure 2:
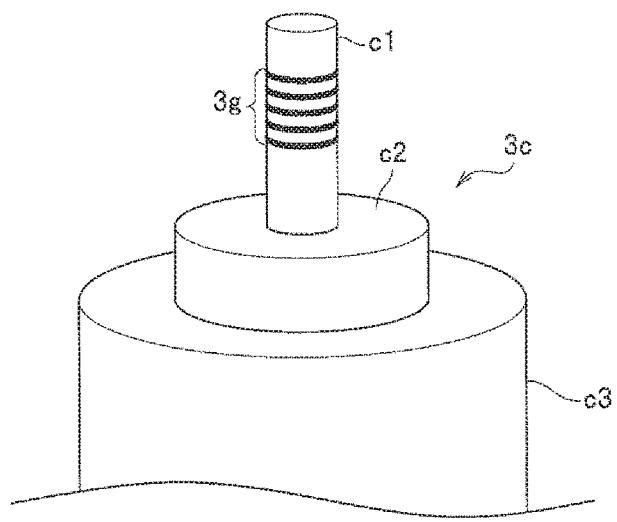
FIG. 2 is an explanatory view of FBG provided in the acoustic emission wave detection system.

FIG. 2 is an explanatory view of the FBG 3c provided in the AE wave detection system S1. The FBG 3c includes a core c1 to be an optical guideway, a clad c2 covering surroundings of the core c1, and a coating c3 covering surroundings of the clad c2 to protect the core c1 and the clad c2.

The core c1 of the FBG 3c includes the diffractive grating 3g (grating) in which the refractive index changes periodically in the axial direction. That is, the diffractive grating 3g is formed in such a way that a location of high refractive index and a location of low refractive index are alternately arranged in the axial direction of the core c1. The diffractive grating 3g is formed by irradiating the core c1 with an interference pattern of ultraviolet rays.

In FIG. 1, the FBG 3c is shown schematically, but in reality, the core c1 including the diffractive grating 3g is covered with the clad c2 and the coating c3 in the axial direction.

As shown in FIG. 1, the FBG 3c is fixed to the housing 3b by adhesion or the like with the lower end q thereof being inserted through the hole h. When the housing 3b is installed on the high-voltage apparatus G, the lower end q of the FBG 3c is close to (or in contact with) the high-voltage apparatus G.

Also, the FBG 3c is fixed to the housing 3b in such a way that the axis thereof is perpendicular to the installation surface r of the housing 3b on the high-voltage apparatus G. This is intended to vibrate the FBG 3c highly sensitively by an AE wave propagating to the surface of the high-voltage apparatus G.

The FBG 3c is fixed to the side of the lower end q inside the housing 3b such that light guided into the housing 3b is received by the upper end p (one end) thereof and an acoustic emission wave from the high-voltage apparatus G is received by the lower end q (the other end) thereof. That is, the FBG 3c is fixed in a cantilever manner inside the housing 3b and the upper end p thereof is spaced from the optical fiber 3a. Thus, by not fixing the upper end p of the FBG 3c, even if the housing 3b is displaced (deformed) accompanying temperature changes or vibrations, the influence thereof is prevented from reaching the FBG 3c and by extension, erroneous detection of an AE wave can be prevented.

Also, the FBG 3c is arranged on the same axis as the optical fiber 3a. That is, the FBG 3c is arranged such that light from the optical fiber 3a is incident on the FBG 3c and light reflected by the diffractive grating 3g is directly incident on the optical fiber 3a. Accordingly, light can be propagated from one of the optical fiber 3a and the FBG 3c to the other.

Figure 3:
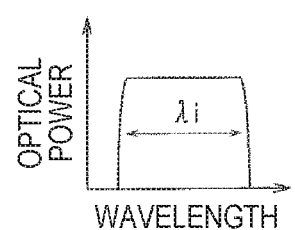
FIG. 3 is an explanatory view of light mutually reinforced by a diffractive grating of FBG.
Figure 3:
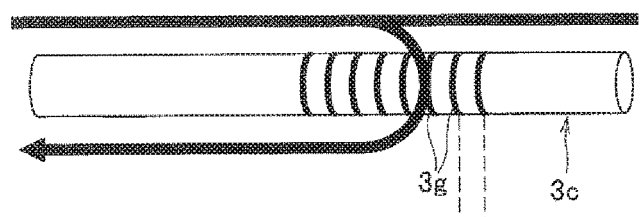
Figure 3:
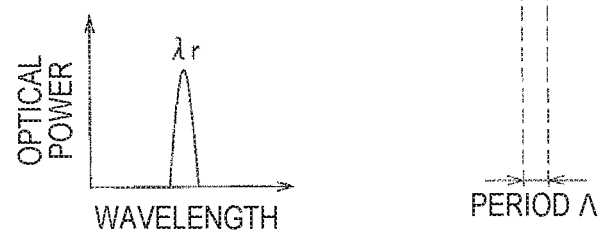

Next, the function of the FBG 3c will be described. FIG. 3 is an explanatory view of light mutually reinforced by the diffractive grating 3g of the FBG 3c.

As shown in FIG. 3, when light of a waveband $\lambda i$ (wideband) is incident on the FBG 3c, the light of a wavelength $\lambda r$ is reflected by the FBG 3c. The wavelength $\lambda r$ of the reflected wave and the period $\Lambda$ (period of duration in which the refractive index changes in the axial direction) of the diffractive grating 3g of the FBG 3c are related by the following (formula 1), where n is an effective refractive index of the FBG 3c.

$$\lambda r = 2n\Lambda \quad \text{(formula 1)}$$

When an AE wave propagates to the FBG 3c, the FBG 3c is vibrated (expanded and contracted in an up and down direction of paper in FIG. 1) by the AE wave to change the period $\Lambda$ (see FIG. 3) of the diffractive grating 3g. If the period $\Lambda$ of the diffractive grating 3g changes, from (formula 1), the wavelength $\lambda r$ of the reflected wave of the FBG 3c also changes. By detecting change of the wavelength $\lambda r$ of the reflected wave, a partial discharge as a sign of a dielectric breakdown can be detected.

The description will continue by returning to FIG. 1.

The optical fiber Fb whose one end is connected to the third port 2c of the optical circulator 2 is an optical device as an optical guideway of light from the FBG 3c toward the optical filter 4. The other end of the optical fiber Fb is connected to the optical filter 4.

The optical filter 4 (first optical filter) is used to extract change of the wavelength $\lambda r$ of the reflected wave of the FBG 3c described above (see FIG. 3) as change of optical power. Here, transmission characteristics of the optical filter 4 will be described with reference to FIGS. 4(a) to 4(c).

Figure 4A:
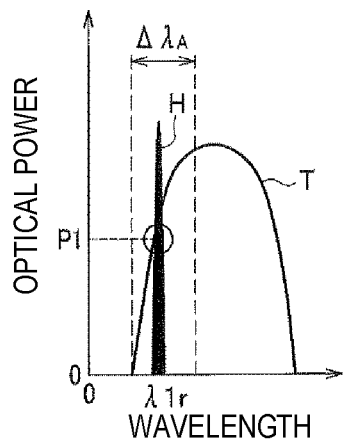
FIGS. 4A-4C are explanatory views showing a relationship between transmission characteristics of an optical filter and a reflected wave of FBG.

FIG. 4(a) is an explanatory view showing the relationship between transmission characteristics T of the optical filter 4 under normal conditions where no AE wave is generated and a reflected wave H of the FBG 3c. The horizontal axis of the explanatory view shown in FIG. 4(a) represents the wavelength of light incident on the optical filter 4 and the vertical axis represents optical power of light passing through the optical filter 4. As shown in FIG. 4(a), the transmission characteristics T of the optical filter 4 have a curved shape that is convex upward.

Under normal conditions where no AE wave is generated, a wavelength $\lambda 1r$ of a reflected wave H (light incident on the optical filter 4 via the optical fibers 3a, Fb) from the FBG 3c and the transmission characteristics T of the optical filter 4 are positionally related as shown in FIG. 4(a). That is, the wavelength $\lambda 1r$ is present in a location where the rate of change of optical power with respect to the wavelength is relatively large (the gradient of the curve is steep) in the transmission characteristics T of the optical filter 4. In other words, the FBG 3c and the optical filter 4 are selected such that the above positional relationship is obtained.

Therefore, if the wavelength $\lambda r$ of the reflected wave from the FBG 3c changes within a wavelength range $\Delta\lambda_A$ (see FIG. 4(a)), optical power of light passing through the optical filter 4 also changes significantly. Accordingly, the expansion and contraction of the FBG 3c accompanying an occurrence of the AE wave can be detected highly sensitively as change of optical power.

The description will continue by returning to FIG. 1 again. The photoelectric converter 5 is used to convert an optical signal (change of optical power) input from the optical filter 4 into an electric signal. The photoelectric converter 5 includes an element that converts an optical signal into an electric signal due to the photoelectric effect such as a photodiode, a phototransistor and the like.

The amplifier 6 is an electronic circuit that includes a bipolar transistor or the like to amplify an electric signal (change of the voltage) input from the photoelectric converter 5.

The AD converter 7 is an electronic circuit that converts an analog signal input from the amplifier 6 into a digital signal. The AD converter 7 has a function to sample an analog signal at a predetermined frequency and to convert a sampled analog signal into a discrete value.

The signal processor 8 is used to determine whether an AE wave is generated in the high-voltage apparatus G and includes electronic circuits such as a central processing unit (CPU), a read only memory (ROM), a random access memory (RAM), and various interfaces. The signal processor 8 also has a function to output a detection result of the AE wave to a display apparatus (not shown) or the like.

Incidentally, a "determination processor" that determines whether an AE wave is generated in the high-voltage apparatus G based on an electric signal input from the photoelectric converter 5 includes the amplifier 6, the AD converter 7, and the signal processor 8 shown in FIG. 1. Processing performed by the signal processor 8 will be described below.

<Operation of the AE Wave Detection System>

Light output from the wideband light source 1 is emitted into the housing 3b via the optical fiber Fa, the optical circulator 2, and the optical fiber 3a. The light emitted into the housing 3b enters the FBG 3c. Light of the wavelength $\lambda r$ satisfying the condition of the (formula 1) described above of light having entered the FBG 3c is reflected after being mutually reinforced by the diffractive grating 3g.

When an AE wave propagates to the FBG 3c accompanying an occurrence of a partial discharge, the diffractive grating 3g of the FBG 3c vibrates and the period $\Lambda$ (see FIG. 3) of the diffractive grating 3g changes. Therefore, the wavelength $\lambda r$ of light reflected after being reinforced by the diffractive grating 3g also changes (wavelength change detection process).

The light reflected by the FBG 3c propagates to the optical filter 4 via the optical fiber 3a, the optical circulator 2, and the optical fiber Fb. Incidentally, light propagating to the housing 3b via the optical fiber 3a and light propagating to the optical filter 4 via the optical fiber 3a after being reflected by the FBG 3c are hardly affected by each other.

As described above, light of optical power P1 (see FIG. 4(a)) corresponding to the wavelength λ1r passes through the optical filter 4 under normal conditions where no partial discharge occurs in the high-voltage apparatus G.

Figure 4B:
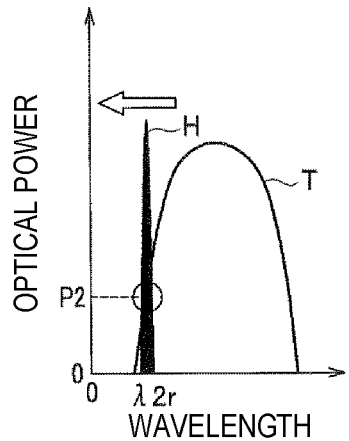

On the other hand, when an AE wave is generated due to a partial discharge in the high-voltage apparatus G and the period Λ of the diffractive grating 3g becomes shorter, a wavelength λ2r of light reflected by the FBG 3c becomes shorter from the above (formula 1) (λ2r<λ1r: see FIGS. 4(a) and 4(b)). Therefore, as shown in FIG. 4(b), optical power P2 of transmitted light of the optical filter 4 becomes smaller than the optical power P1 under normal conditions (see FIG. 4(a)) (P2<P1).

Figure 4C:
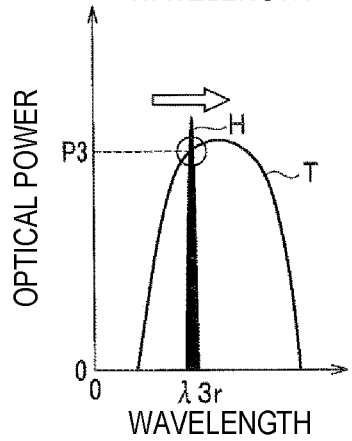

When the period Λ of the diffractive grating 3g becomes longer due an AE wave, a wavelength λ3r of light reflected by the FBG 3c becomes longer from the above (formula 1) (λ3r>λ1r: see FIGS. 4(a) and 4(c)). Therefore, as shown in FIG. 4(c), optical power P3 of transmitted light of the optical filter 4 becomes smaller than the optical power P1 under normal conditions (see FIG. 4(a)) (P3<P1).

Thus, the FBG 3c vibrates due to an AE wave and, accompanying the vibration of the FBG 3c, optical power of transmitted light of the optical filter 4 changes sensitively (optical power conversion process).

Change of optical power of transmitted light of the optical filter 4 is converted into change of the voltage by the photoelectric converter 5 (photoelectric conversion process). The change of the voltage is amplified by the amplifier 6. The voltage input from the amplifier 6 is converted into a digital signal by the AD converter 7 and the digital signal is input into the signal processor 8.

The signal processor 8 determines whether an AE wave arises in the high-voltage apparatus G based on the digital signal input from the AD converter 7 (determination process). For example, the signal processor 8 determines that "a partial discharge is detected" if the width of change of the digital signal input from the AD converter 7 is equal to a predetermined threshold or more.

Incidentally, the signal processor 8 may determine that "a partial discharge is detected" if the number of times (that is, the frequency) that the width of change of the digital signal becomes equal to the predetermined threshold or more becomes equal to a predetermined value or more in a unit time.

The signal processor 8 outputs a determination result thereof to a notification means (a display, a buzzer or the like: not shown). That is, the signal processor 8 notifies the user that a partial discharge arose in the high-voltage apparatus G and it is highly probable that a dielectric breakdown will occur through the notification means. Accordingly, the user grasps that a partial discharge arose in the high-voltage apparatus G and can maintain the high-voltage apparatus G before a dielectric breakdown occurs.

Effect

According to the present embodiment, the AE wave detector 3 can be installed close to (in contact with) the high-voltage apparatus G whose dielectric breakdown is worried about. This is because the FBG 3c is superior in insulation resistance and is not subject to discharges and noise from the high-voltage apparatus G.

Figure 15:
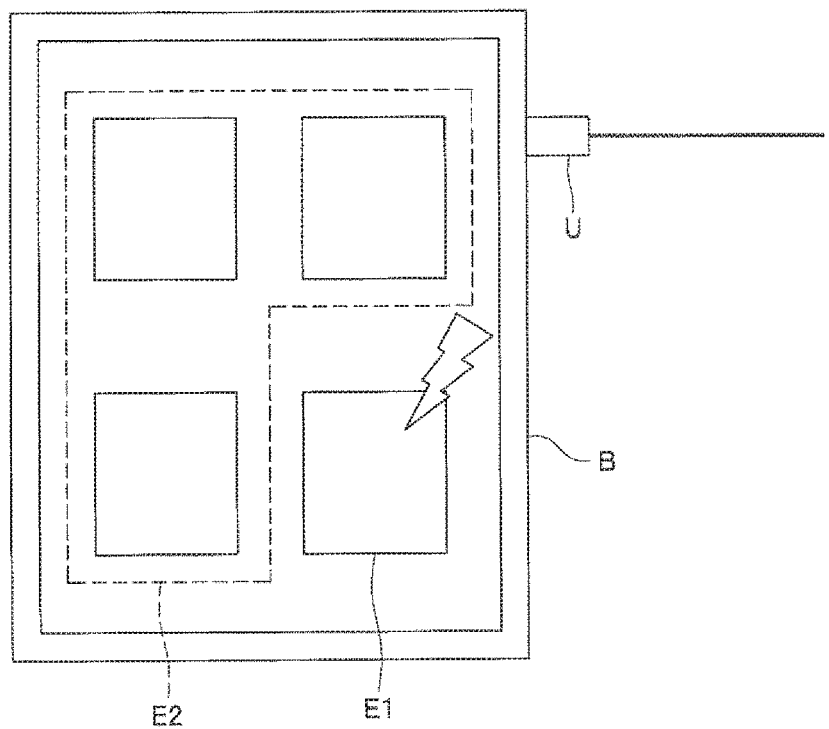
FIG. 15 is an explanatory view showing a state in which an AE sensor according to a comparative example is installed in a container.

FIG. 15 is an explanatory view showing a state in which an AE sensor U according to a comparative example is installed in a container B. In the example shown in FIG. 15, the AE sensor U using the piezoelectric effect is installed in the container B housing a high-voltage apparatus E1. This is intended to prevent, superposition of discharges and noise from the high-voltage apparatus E1.

If an AE wave is indirectly detected via the container B as described above, an AE wave attenuated in the process of propagating through the container B is detected by the AE sensor U. Also, the AE wave propagates to various devices E2 including the container B and thus, the propagation path before reaching the AE sensor U becomes complicated, posing a problem of decreased precision of detection of the AE sensor U.

According to the present invention, by contrast, the FBG 3c (see FIG. 1) is superior in insulation resistance and thus, the AE wave detector 3 can be installed directly on the high-voltage apparatus G. In addition, an AE wave propagates to the FBG 3c before propagating to devices other than the high-voltage apparatus G. Therefore, a digital signal reflecting the shape of an AE wave correctly (photoelectrically converted signal) can be acquired so that an AE wave can be detected highly sensitively by the AE wave detector 3.

The FBG 3c (see FIG. 1) is fixed in a cantilever manner inside the housing 3b and thus, the FBG 3c can be prevented from being pulled or compressed due to deformation of vibration of the housing 3b.

Figure 16:
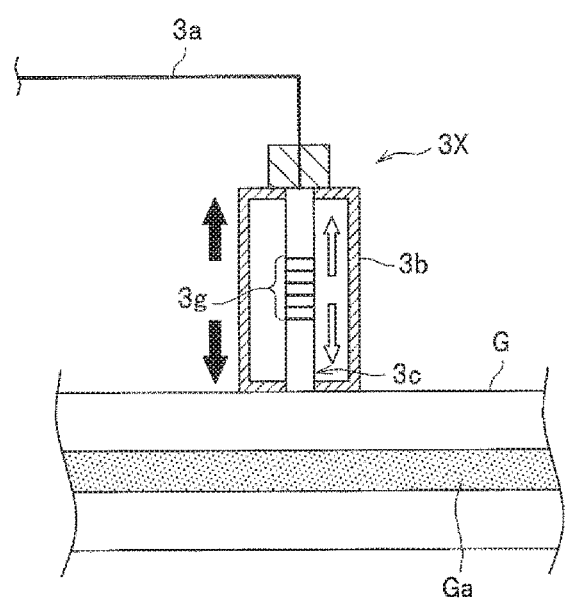
FIG. 16 is a sectional view of an acoustic emission wave detector according to a comparative example.

FIG. 16 is a sectional view of an AE wave detector 3X according to a comparative example. In the comparative example shown in FIG. 16, both ends of the FBG 3c are fixed to the housing 3b. In such a configuration, it is difficult to determine whether the change of wavelength of a reflected wave from the FBG 3c is caused by an AE wave during partial discharge, or pulling or compression by the housing 3b.

According to the present invention, by contrast, as described above, the FBG 3c (see FIG. 1) is fixed in a cantilever manner inside the housing 3b and thus, the FBG 3c can be prevented from expanding or contracting accompanying deformation or the like of the housing 3b. Therefore, the precision of detection of an AE wave by the AE wave detector 3 can be improved.

The FBG 3c is fixed to the housing 3b in such a way that the axis thereof is perpendicular to the installation surface r of the housing 3b on the high-voltage apparatus G. Thus, if the high-voltage apparatus G is, for example, a high-voltage line, an AE wave propagating in the radial direction (up and down direction in FIG. 1) of the high-voltage line also propagates directly to FBG 3c. Therefore, an AE wave accompanying a partial discharge in the high-voltage apparatus G can be detected highly sensitively by the AE wave detector 3.

Second Embodiment

The second embodiment is different from the first embodiment in that a laser diode 1A (see FIG. 5) is used, instead of the wideband light source 1 (see FIG. 1), and the optical filter 4 (see FIG. 1) is omitted and is otherwise the same as the first embodiment. Thus, a different portion from the first embodiment will be described and the description of overlapping portions is omitted.

Figure 5:
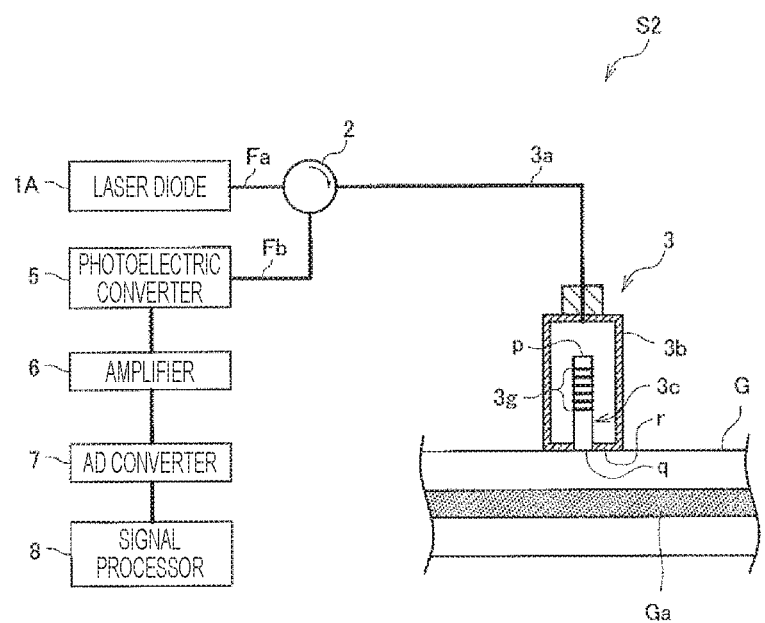
FIG. 5 is a schematic diagram of an acoustic emission wave detection system according to a second embodiment of the present invention.

FIG. 5 is a schematic diagram of an AE wave detection system S2 according to the second embodiment. The AE wave detection system S2 includes the laser diode 1A, the optical circulator 2, the AE wave detector 3, the photoelectric converter 5, the amplifier 6, the AD converter 7, and the signal processor 8.

The laser diode 1A (light source) is a light source that emits light of a predetermined wavelength $\lambda_{LD}$ (light whose wavelength band is very narrow). The laser diode 1A is arranged in such a way that light is emitted toward one end of the optical fiber Fa.

Figure 6A:
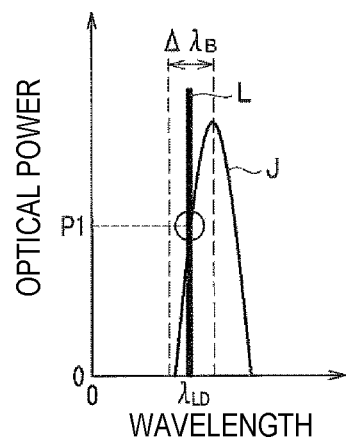
FIGS. 6A-6C are explanatory views showing a relationship between a reflectance distribution of FBG and light emitted from a laser diode.

FIG. 6(a) is an explanatory view showing a relationship between a reflectance distribution J of the FBG 3c under normal conditions where no AE wave is generated and light L emitted from the laser diode 1A. Reference sign L shown in FIG. 6(a) represents the wavelength $\lambda_{LD}$ and optical power of light emitted from the laser diode 1A. The reflectance distribution J of the FBG 3c has curved shape that is convex upward.

The reflectance distribution J shown in FIG. 6(a) corresponds to the reflected wave H of FIG. 4(a) described in the first embodiment. That is, the change of wavelength of the reflected wave H of the FBG 3c described in the first embodiment (see FIGS. 4(b) and 4(c)) is due to change of the reflectance distribution J (see FIGS. 6(a) to 6(c)) of the FBG 3c.

Under normal conditions where no AE wave is generated, the wavelength $\lambda_{LD}$ of the light L from the laser diode 1A and the reflectance distribution J of the FBG 3c are positionally related as shown in FIG. 6(a). That is, the wavelength $\lambda_{LD}$ is present in a location where the rate of change of optical power with respect to the wavelength is relatively large (the gradient of the curve is steep) in the reflectance distribution J of the FBG 3c. In other words, the laser diode 1A and the FBG 3c are selected such that the above positional relationship is obtained.

Therefore, if the reflectance distribution J of the FBG 3c changes within a wavelength range $\Delta\lambda_B$ (see FIG. 6(a)), optical power of light mutually reinforced by being reflected by the FBG 3c also changes significantly. Accordingly, the expansion and contraction of the FBG 3c accompanying an occurrence of the AE wave can be detected highly sensitively as change of optical power.

<Operation of the AE Wave Detection System>

When an AE wave propagates to the FBG 3c accompanying an occurrence of a partial discharge, the diffractive grating 3g of the FBG 3c vibrates (expands and contracts) and also the reflectance distribution J (see FIG. 6(a)) of the diffractive grating 3g changes.

Figure 6B:
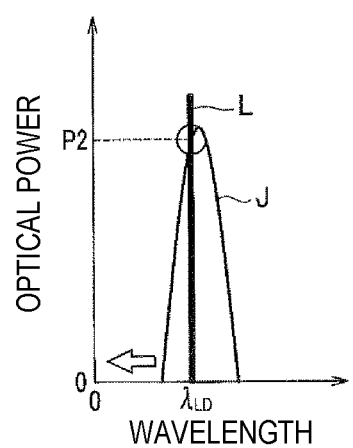

If the period Λ of the diffractive grating 3g becomes shorter, the reflectance distribution J of the FBG 3c shifts to the shorter wavelength side from the above (formula 1) (see an arrow in FIG. 6(b)). Incidentally, the wavelength $\lambda_{LD}$ of the light L emitted from the laser diode 1A is constant. Thus, as shown in FIG. 6(b), the optical power P2 of light mutually reinforced by being reflected by the FBG 3c becomes larger than the optical power P1 under normal conditions (see FIG. 6(a)) (P2>P1).

Figure 6C:
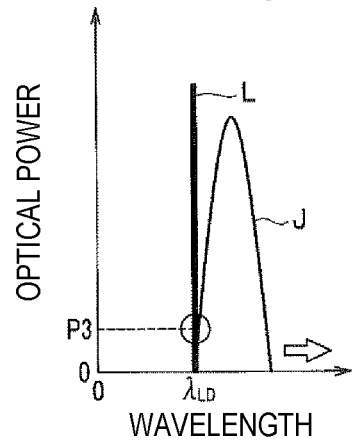

If the period Λ of the diffractive grating 3g becomes longer, the reflectance distribution J of the FBG 3c shifts to the longer wavelength side from the above (formula 1) (see an arrow in FIG. 6(c)). Thus, as shown in FIG. 6(c), the optical power P3 of light mutually reinforced by being reflected by the FBG 3c becomes smaller than the optical power P1 under normal conditions (see FIG. 6(a)) (P3<P1).

In this manner, the FBG 3c vibrates due to an AE wave and optical power of light mutually reinforced by being reflected by the FBG 3c changes (optical power conversion process). The change of optical power is converted into an electric signal by the photoelectric converter 5 shown in FIG. 5 (photoelectric conversion process) and the electric signal is amplified by the amplifier 6.

The process (determination process) performed by the AD converter 7 and the signal processor 8 is the same as in the first embodiment and so the description thereof is omitted.

Effect

According to the present embodiment, an AE wave can be detected highly sensitively by using the fact that the reflectance distribution J (see FIGS. 6(a) to 6(c)) of the FBG 3c changes accompanying an occurrence of an AE wave. Also, the optical filter 4 (see FIG. 1) described in the first embodiment becomes unnecessary and therefore, the cost needed for the AE wave detection system S2 can be reduced.

Third Embodiment

The third embodiment is different from the first embodiment in that an AE wave detector 3A (see FIG. 7) includes an optical connector 3d and is otherwise the same as the first embodiment. Thus, a different portion from the first embodiment will be described and the description of overlapping portions is omitted.

Figure 7:
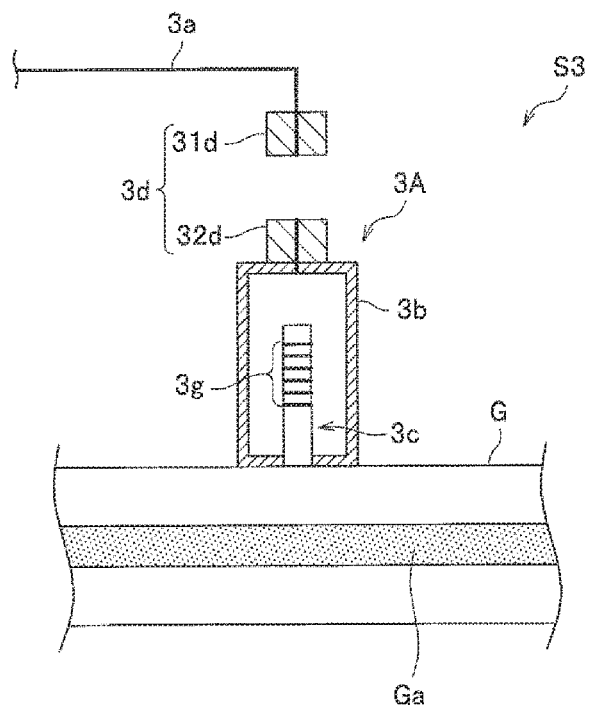
FIG. 7 is a schematic diagram of an acoustic emission wave detector provided in an acoustic emission wave detection system according to a third embodiment of the present invention.

FIG. 7 is a schematic diagram of an AE wave detector 3A included in an AE wave detection system S3 according to the third embodiment. In FIG. 7, a state in which an optical plug 31d is pulled from an optical receptacle 32d is illustrated.

The optical connector 3d is used to allow the optical fiber 3a to be inserted into/removed from the housing 3b. The optical connector 3d includes the optical plug 31d installed near one end of the optical fiber 3a and the optical receptacle 32d installed on the housing 3b.

The optical plug 31d and the optical receptacle 32d are configured to be mutually insertable/removable. The optical receptacle 32d includes, like the optical fiber 3a, a core and a clad. Then, the FBG 3c is irradiated with light via the optical fiber 3a and the optical connector 3d and light reflected by the FBG 3c propagates through the optical connector 3d and the optical fiber 3a.

Effect

According to the present embodiment, the optical fiber 3a can be removed from the housing 3b by pulling out the optical plug 31d from the optical receptacle 32d. When mounting the AE wave detector 3A on the high-voltage apparatus G, the optical plug 31d may be inserted into the optical receptacle 32d after the housing 3b being mounted on the high-voltage apparatus G. Therefore, the mounting work of the AE wave detector 3A can easily be done.

Fourth Embodiment

The fourth embodiment is different from the first embodiment in that a mirror 3i (see FIG. 8) and a holding member 3j (see FIG. 8) are in eluded inside the housing 3b and is otherwise the same as the first embodiment. Thus, a different portion from the first embodiment will be described and the description of overlapping portions is omitted.

Figure 8:
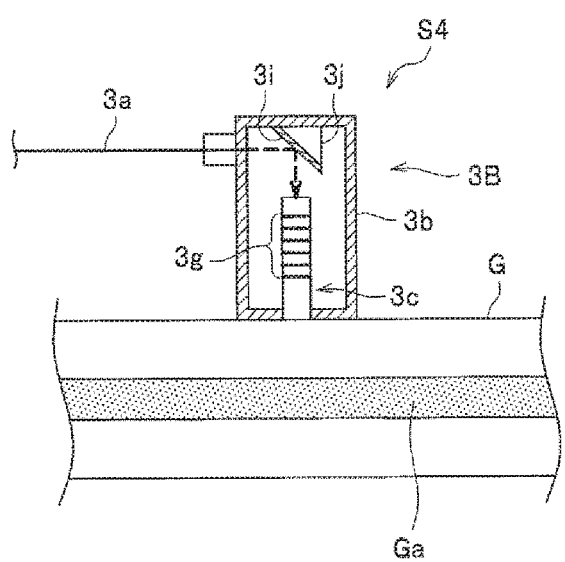
FIG. 8 is a schematic diagram of an acoustic emission wave detector provided in an acoustic emission wave detection system according to a fourth embodiment of the present invention.

FIG. 8 is a schematic diagram of an AE wave detector 3B included in an AE wave detection system S4 according to the fourth embodiment.

The mirror 3i (mirror member) is used to reflect light emitted from the optical fiber 3a toward the FBG 3c and also to reflect light mutually reinforced by the diffractive grating 3g of the FBG 3c toward the optical fiber 3a and is installed inside the housing 3b.

The holding member 3j to hold the mirror 3i in an inclined state of a predetermined angle (for example, 45° in a longitudinal section view) with respect to the top wall is installed on the ceiling surface of the housing 3b. The mirror 3i is installed on the inclined plane of the holding member 3j. Also, the optical fiber 3a is inserted through a hole (not shown) provided in the sidewall of the housing 3b so that the above reflection occurs on the mirror 3i.

Effect

According to the present embodiment, the mirror 3i is installed inside the housing 3b and the optical fiber 3a is inserted into a hole in the side wall of the housing 3b and thus, the AE wave detector 3B can be made lower than in the first embodiment (see FIG. 1). Therefore, if, for example, there is not enough space in the height direction of the high-voltage apparatus G (up and down direction of paper in FIG. 8), the AE wave detector 3B can easily be installed on the high-voltage apparatus G.

Fifth Embodiment

The fifth embodiment is different from the first embodiment in that an optical coupler K (see FIG. 9) that demultiplexes light emitted from the wideband light source 1 is included and a plurality of detection units (AE wave detectors 31, 32, . . . , 3n: see FIG. 9) is included and is otherwise the same as the first embodiment. Thus, a different portion from the first embodiment will be described and the description of overlapping portions is omitted.

Figure 9:
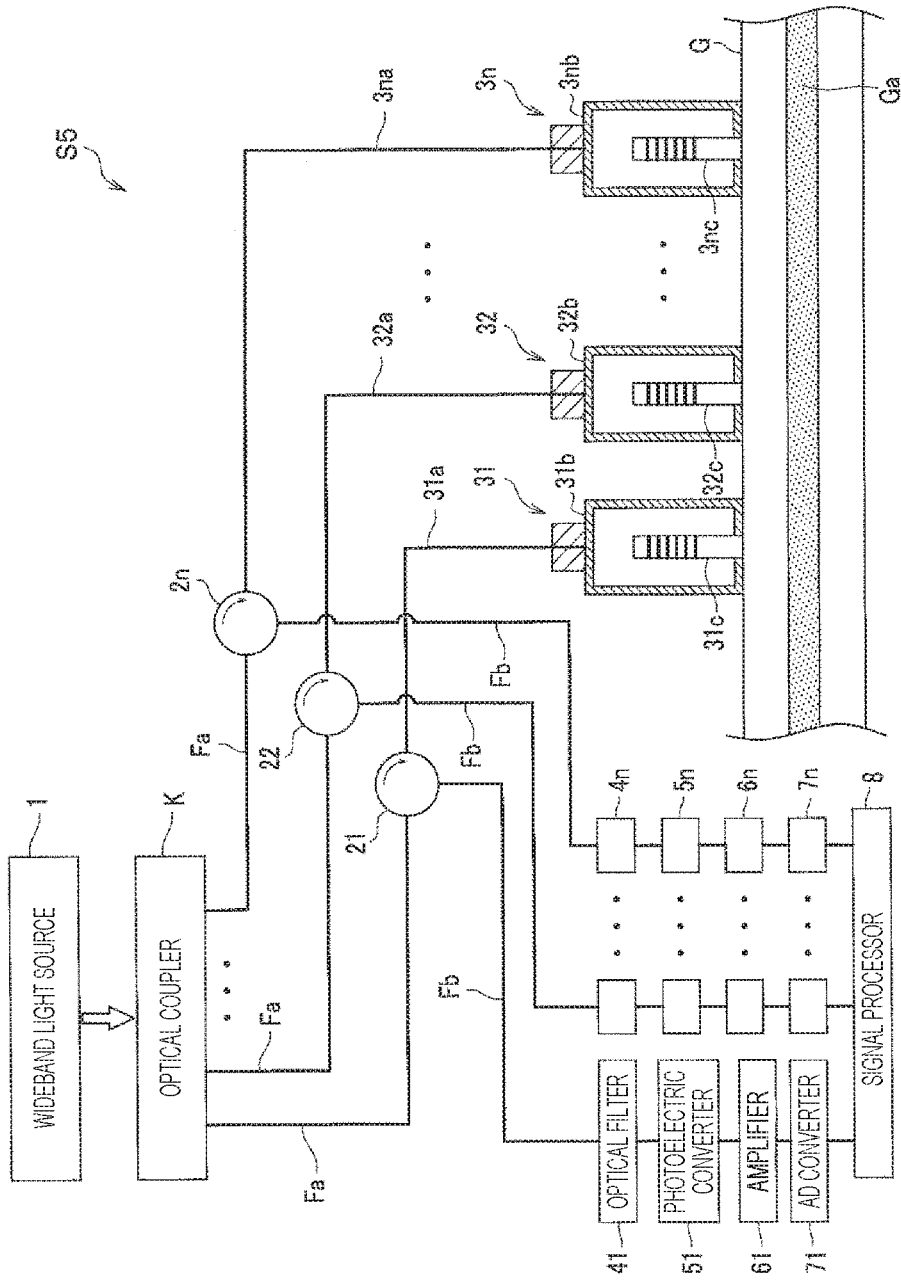
FIG. 9 is a schematic diagram of an acoustic emission wave detection system according to a fifth embodiment of the present invention.

FIG. 9 is a schematic diagram of an AE wave detection system S5 according to the fifth embodiment. The AE wave detection system S5 includes the wideband light source 1, the optical coupler K, n detection units (the AE wave detectors 31, 32, . . . , 3n), and the signal processor 8.

The optical coupler K is an optical device to demultiplex light emitted from the wideband light source 1. n optical fibers Fa to allow demultiplexed light to propagate toward the AE wave detectors 31, 32, . . . , 3n are connected to the optical coupler.

The first detection unit includes an optical circulator 21, an AE wave detector 31, an optical filter 41, a photoelectric converter 51, an amplifier 61, and an AD converter 71. Incidentally, the configuration and connection relations of each device described above are similar to those in the first embodiment and thus, the description thereof is omitted.

The AE wave detection system S5 includes n detection units described above. If the high-voltage apparatus G is, for example, a high-voltage line, the n AE wave detectors 31, 32, . . . , 3n are installed along the axial direction of the high-voltage line.

The signal processor 8 determines whether a partial discharge has occurred in the high-voltage apparatus G based on digital signals input from AD converters 71, 72, . . . , 7n. If, for example, a partial discharge is detected by at least one detection unit, the signal processor 8 outputs a message to the notification means (not shown) that a partial discharge has occurred.

Incidentally, information about the installation position of the housing 3b may be stored in a storage unit (not shown) of the signal processor 8 so as to identify the location of occurrence of a partial discharge based on propagation times of an AE wave to AE wave detectors 31, 32, . . . , 3n. For example, the location of occurrence of a partial discharge can be identified based on the distances between detection units and differences of detection times of an AE wave by the detection units.

Effect

According to the present embodiment, a plurality of the AE wave detectors 31, 32, . . . , 3n is installed on the high-voltage apparatus G and thus, a partial discharge can be detected in a plurality of locations on the high-voltage apparatus. Also, the location of occurrence of a partial discharge can be identified based on propagation times of an AE wave to the AE wave detectors 31, 32, . . . , 3n.

Sixth Embodiment

The sixth embodiment is different from the second embodiment in that a plurality of detection units (AE wave detectors 31, 32, . . . , 3n: see FIG. 10) is included and optical multiplexers M1, M2 and optical demultiplexers N1, N2 are included and is otherwise the same as the second embodiment (see FIG. 5). Thus, a different portion from the second embodiment will be described and the description of overlapping portions is omitted.

Figure 10:
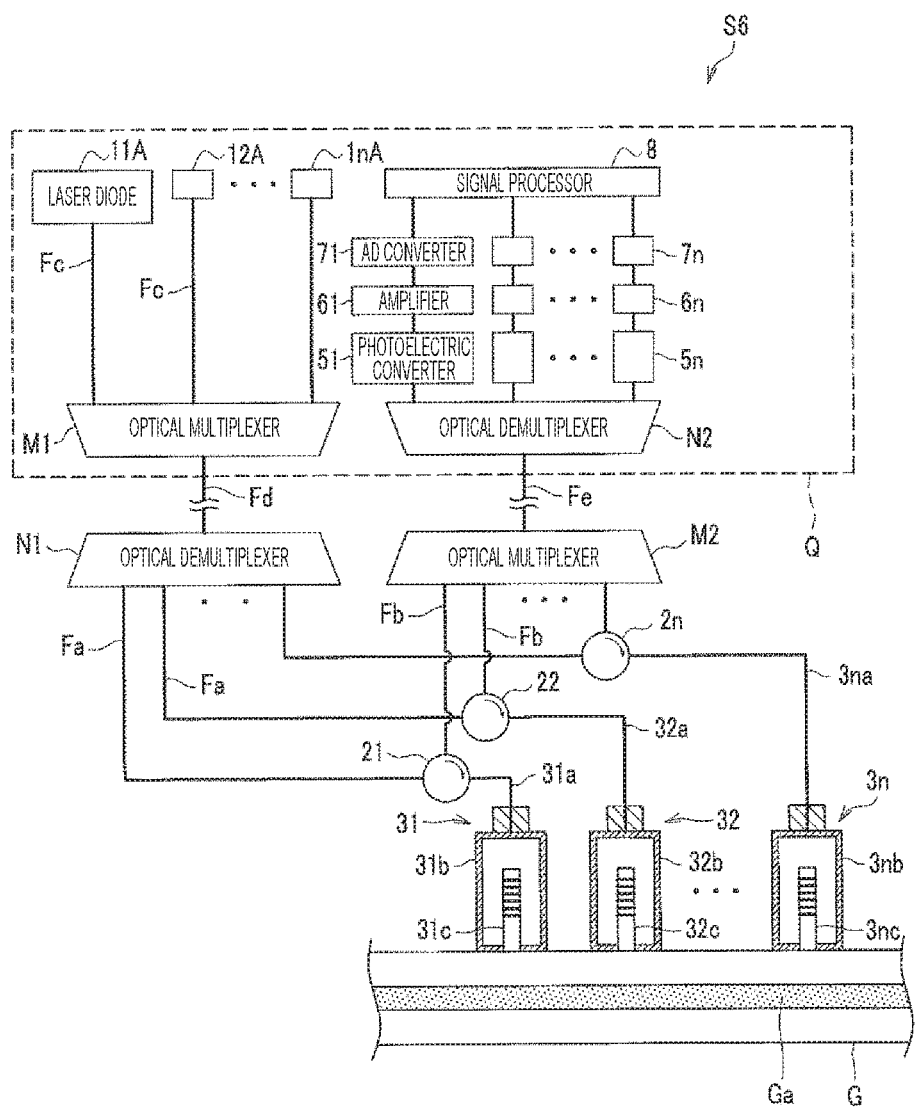
FIG. 10 is a schematic diagram of an acoustic emission wave detection system according to a sixth embodiment of the present invention.

FIG. 10 is a schematic diagram of an AE wave detection system S6 according to the sixth embodiment. In FIG. 10, a broken line frame indicated by reference sign Q represents a monitoring chamber that monitors for an occurrence of a partial discharge.

The AE wave detection system S6 includes n detection units (AE wave detectors 31, 32, . . . , 3n), the optical multiplexers M1, M2, the optical demultiplexers N1, N2, and the signal processor 8.

The first detection unit includes a laser diode 11A, the optical circulator 21, the AE wave detector 31, the photoelectric converter 51, the amplifier 61, and the AD converter 71.

The laser diode 11A is a light source that emits light of the wavelength $\lambda 1_{LD}$ toward an optical fiber Fc. Incidentally, lights of different wavelengths $\lambda 1_{LD}, \lambda 2_{LD}, \ldots, \lambda n_{LD}$ are emitted by n laser diodes 11A, 12A, . . . 1nA.

The configuration of the first detection unit is similar to that of the second embodiment and thus, the description thereof is omitted. Also, the description of other detection units is omitted.

The optical multiplexer M1 is an optical device that multiplexes lights of the wavelengths $\lambda 1_{LD}, \lambda 2_{LD}, \ldots, \lambda n_{LD}$ propagating through n optical fibers Fc and emits the multiplexed light to an optical fiber Fd.

The optical fiber Fd is an optical device serving as an optical guideway of the light multiplexed by the optical multiplexer M1. One end of the optical fiber Fd is connected to the optical multiplexer M1 and the other end thereof is connected to the optical demultiplexer N1.

The optical demultiplexer M1 is an optical device that demultiplexes light incident from the optical multiplexer M1 via the optical fiber Fd into lights of the wavelengths $\lambda 1_{LD}, \lambda 2_{LD}, \lambda n_{LD}$ for each of a plurality of wavebands and emits the demultiplexed lights into the n optical fibers Fa.

Figure 11:
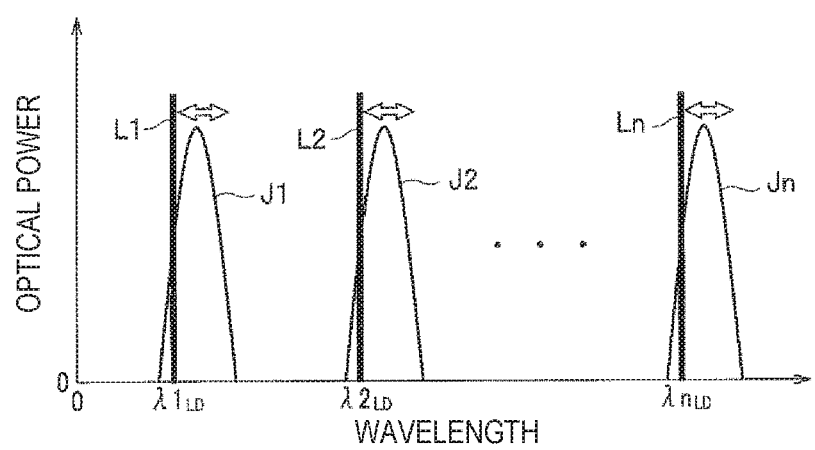
FIG. 11 is an explanatory view showing the relationship between the reflectance distribution of FBG and light emitted from the laser diode.

Next, characteristics of each of FBG 31c, 32c, . . . , 3nc will be described. FIG. 11 is an explanatory view showing the relationship between the reflectance distributions of the FBG 31c, 32c, . . . , 3nc and lights L1, L2, . . . , Ln emitted from the laser diodes 11A, 12A, . . . , 1nA.

Reference sign Lk in FIG. 11 (hereinafter, k=1, 2, ..., n) represents the wavelength $\lambda k_{LD}$ and optical power of light emitted from the laser diode 1kA. Reference sign Jk represents the reflectance distribution of the FBG 3kc in a state in which no partial discharge occurs in the high-voltage apparatus G.

In the reflectance distribution Jk shown in FIG. 11, the wavelength at which the optical power of a reflected wave takes the maximum value is different from each other. The wavelength $\lambda k_{LD}$ of the laser diode 1kA is set by associating with the reflectance distribution Jk. That is, the FBG 3kc and the laser diode 1kA are selected such that when the reflectance distribution Jk changes accompanying expansion or contraction of the FBG 3kc (see an arrow in FIG. 11), the optical power of a reflected wave of the FBG 3kc changes significantly.

The optical multiplexer M2 shown in FIG. 10 is an optical device that multiplexes n lights of the wavelengths $\lambda k_{LD}$ propagating via the optical fiber Fb after being reflected by the FBG 3kc and emits the multiplexed light to an optical fiber Fe.

The optical fiber Fe is an optical device serving as an optical guideway of the light multiplexed by the optical multiplexer M2. One end of the optical fiber Fe is connected to the optical multiplexer M2 and the other end thereof is connected to the optical demultiplexer N2.

The optical demultiplexer N2 is an optical device that demultiplexes light incident from the optical multiplexer M2 via the optical fiber Fe into lights of a plurality of wavelengths $\lambda k_{LD}$ for a plurality of wavebands and emits the demultiplexed lights into a photoelectric converter 5k.

The signal processor 8 determines whether a partial discharge has occurred in the high-voltage apparatus G based on digital signals input from n AD converters 7k. The process performed by the signal processor 8 is similar to that in the fifth embodiment and thus, the description thereof is omitted.

Effect

According to the present embodiment, a partial discharge can be detected in a plurality of locations by installing n AE wave detectors 3k on the high-voltage apparatus G. Also, if, for example, the monitoring chamber Q is located away from the high-voltage apparatus G, the number of optical fibers (two optical fibers Fd, Fe) routed to the monitoring chamber Q can be made smaller than that in the fifth embodiment so that installation costs can be reduced.

Seventh Embodiment

The seventh embodiment is different from the sixth embodiment in that an optical filter 31f (see FIG. 12) is installed inside a housing 31b (see FIG. 12) and the AE wave detectors 31, 32, ..., 3n are connected in series via optical fibers 31a, 32a, ..., 3na and is otherwise the same as the sixth embodiment. Thus, a different portion from the sixth embodiment will be described and the description of overlapping portions is omitted.

Figure 12:
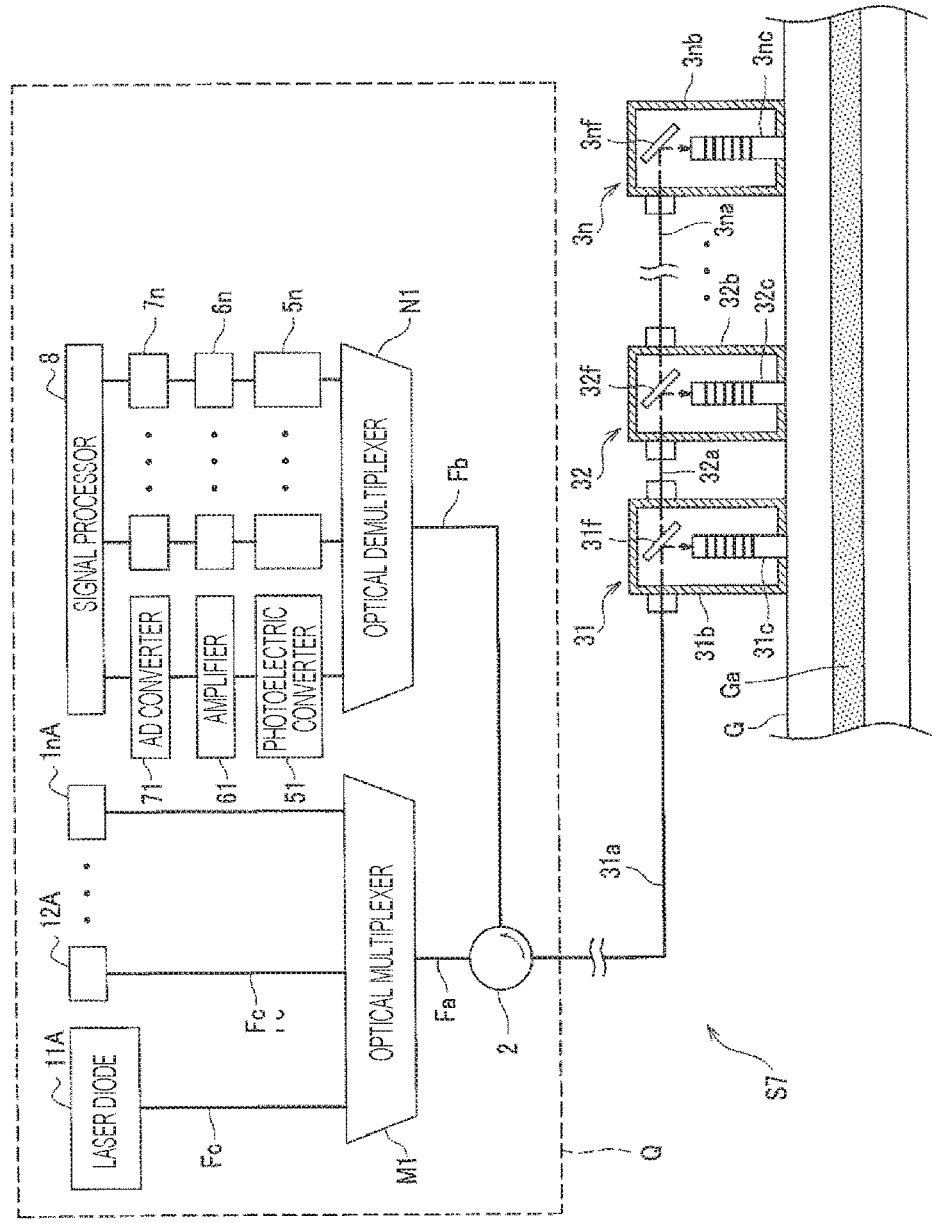
FIG. 12 is a schematic diagram of an acoustic emission wave detection system according to a seventh embodiment of the present invention.

FIG. 12 is a schematic diagram of an AE wave detection system S7 according to the seventh embodiment. The AE wave detection system S7 includes n detection units (AE wave detectors 31, 32, ..., 3n), the optical multiplexer M1, the optical circulator 2, the optical demultiplexer N1, and the signal processor 8.

The optical circulator 2 (optical guideway forming device) is an optical device that allows light from the optical multiplexer M1 to the FBG 3kc via the optical fiber 3ka (k=1, 2, ..., n) to propagate and also allows light to the optical demultiplexer N1 via the optical fiber 3ka after being reflected by the diffractive grating 3kg to propagate.

The first detection unit includes the laser diode 11A, the AE wave detector 31, the photoelectric converter 51, the amplifier 61, and the AD converter 71.

The laser diode 11A is a light source that emits light of the wavelength $\lambda 1_{LD}$ (see FIG. 11) toward the optical fiber Fc. Incidentally, lights of different wavelengths $\lambda 1_{LD}$, $\lambda 2_{LD}$, ..., $\lambda n_{LD}$ are emitted by n laser diodes 11A, 12A, ..., 1nA.

The AE wave detector 31 includes the optical fiber 31a, the housing 31b, the FBG 31c, and the optical filter 31f.

Two holes (not shown) are provided in the sidewall of the housing 31b and the optical fiber 31a is inserted through one hole and the optical fiber 32a is inserted through the other hole. Then, a portion of light emitted from one of the optical fibers 31a, 32a enters the other by passing through the optical filter 31f described below.

The optical filter 31f (second optical filter) is used to allow light of a wavelength region including the wavelength $\lambda 1_{LD}$ of the laser diode 11A to reflect and allows light of wavelengths not included in the wavelength region to pass through. The optical filter 31f is arranged on a path of light from one of the optical fibers 31a, 32a to the other inside the housing 31b.

The optical filter 31f is arranged in an inclined state of a predetermined angle (for example, 45°) with respect to the top wall of the housing 31b. This is intended to allow a portion of light incident from the optical fiber 31a to propagate to the FBG 31c after being reflected by the optical filter 31f and light mutually reinforced by the diffractive grating of the FBG 31c to propagate to the optical fiber 31a after being reflected by the optical filter 31f.

The FBG 31c has, like in the sixth embodiment (see FIG. 11l), a reflectance distribution corresponding to the wavelength $\lambda 1_{LD}$ of the laser diode 11A. That is, when the reflectance distribution changes accompanying expansion or contraction of the FBG 31c (see an arrow in FIG. 11), optical power of a reflected wave (wavelength $\lambda 1_{LD}$) mutually reinforced by the diffractive grating also changes significantly.

As shown in FIG. 12, one end of the optical fiber 32a is connected to the housing 31b of the AE wave detector 31 and the other end is connected to the housing 32b of the AE wave detector 32. In this manner, n AE wave detectors 3k (k=1, 2, ..., n) are connected in series via the optical fiber 3(k+1)a such that light having passed through the optical filter 3kf enters the housing 3(k+1)b of another detection unit.

Light of the wavelength $\lambda k_{LD}$ of light incident on the housing 3kb via the optical fiber 3ka propagates to the FBG 3kc after being reflected by the optical filter 3kf. Lights of wavelengths other than the wavelength $\lambda k_{LD}$ of light entering the housing 3kb pass through the optical filter 3kf and the light having passed through enters the housing 3(k+1)b via the optical fiber 3(k+1)a. In this manner, light of the wavelength $\lambda k_{LD}$ is successively demultiplexed from light multiplexed by the optical multiplexer M1.

Light having been mutually reinforced by the FBG 3kc propagates in the opposite direction of the above path. That is, light of the wavelength $\lambda k_{LD}$ having been mutually reinforced by the FBG 3kc is reflected by the optical filter 3kf and the reflected light propagates to the housing 3(k−1)b via the optical fiber 3ka. The light passes through the optical filter 3(k−1)f installed inside the housing 3(k−1)b before entering the optical fiber 3(k−2). In this manner, light of the wavelength $\lambda k_{LD}$ is successively joined. The joined light propagates to the optical demultiplexer N1 via the optical fiber 31a, the optical circulator 2, and the optical fiber Fb.

Other components such as the signal processor 8 are the same as in the sixth embodiment and thus, the description thereof is omitted.

<Effect>

According to the present embodiment, a partial discharge can be detected in a plurality of locations by installing n AE wave detectors 3k on the high-voltage apparatus G. Also, the AE wave detectors 3k are configured to be connected in series by one line (optical fiber 3ka). Thus, one unit of the optical circulator 2 is sufficient and there is no need to provide, like in the sixth embodiment, a plurality of the optical circulators 21 (see FIG. 10) and the like. Therefore, connection relations of the AE wave detectors 3k can be simplified and also the costs needed for the optical fiber 3ka and the circulator 2 can be reduced.

Modification

In the foregoing, each embodiment of the AE wave detector system S1 and the like according to the present invention has been described, but the present invention is not limited to these descriptions and various alterations can be made.

Figure 13:
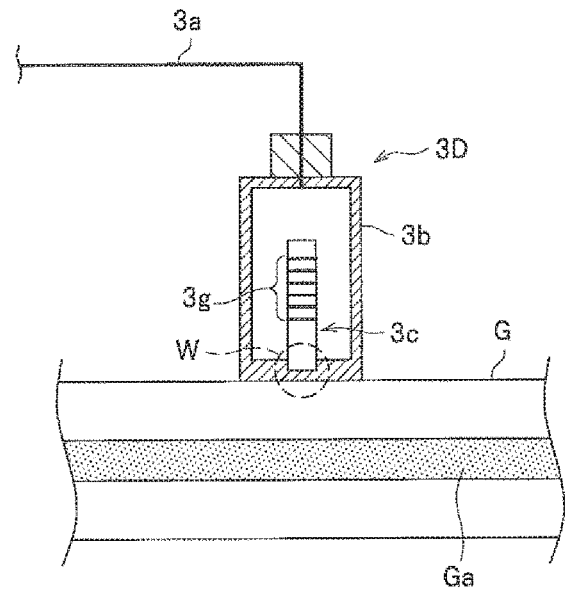
FIG. 13 is a schematic diagram of an acoustic emission wave detector provided in an acoustic emission wave detection system according to a modification of the present invention.

In the first embodiment (see FIG. 1), for example, a configuration that exposes the lower end q (the other end) of the FBG 3c via the hole h provided in the bottom wall of the housing 3b has been described, but the present invention is not limited to such an example. That is, as shown in FIG. 13, the lower end q of the FBG 3c may be fixed to the bottom wall without providing a hole in the bottom wall of the housing 3b (see an area W). Even in such a configuration, an AE wave accompanying a partial discharge propagates to the FBG 3c via the bottom wall of the housing 3b so that a partial discharge can be detected using the vibration of the FBG 3c.

Figure 14:
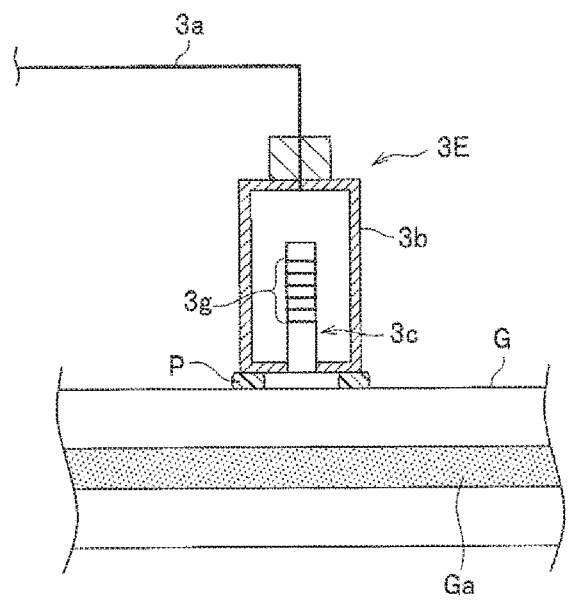
FIG. 14 is a schematic diagram of an acoustic emission wave detector provided in an acoustic emission wave detection system according to another modification of the present invention.

In the first embodiment (see FIG. 1), a case in which the bottom wall of the housing 3b is brought into contact with the high-voltage apparatus G has been described, but the present invention is not limited to such an example. For example, as shown in FIG. 14, the housing 3b may be mounted on the high-voltage apparatus G via a UV curable resin P such as resin. In such a case, the UV curable resin P is applied to the bottom wall of the housing 3b and the UV curable resin P is cured by irradiating the housing 3b with ultraviolet rays while the housing 3b is mounted on the high-voltage apparatus G. Accordingly, the housing 3b can easily be mounted on, for example, a curved portion where a partial discharge is more likely to occur of the high-voltage line (high-voltage apparatus G).

Also in the first embodiment (see FIG. 1), a case in which the axis of the FBG 3c is perpendicular to the installation surface r of the housing 3b on the high-voltage apparatus G has been described, but the present invention is not limited to such an example. That is, the FBG 3c may be installed in an inclined state in which the axis thereof is inclined a predetermined angle with respect to the installation surface r of the housing 3b on the high-voltage apparatus G.

In the fifth embodiment (see FIG. 9), a configuration in which light incident from the wideband light source 1 is demultiplexed by the optical coupler K has been described, but the present invention is not limited to such an example. That is, the wideband light source 1 may be provided on the one-end side of each of a plurality of optical fibers Fa.

In the sixth embodiment (see FIG. 10), a configuration in which the AE wave detection system S6 includes the optical multiplexers M1, M2 and the optical demultiplexers N1, N2 has been described, but the present invention is not limited to such an example. For example, lights from the laser diodes 11A, 12A, . . . , 1nA may directly enter n optical fibers Fa by omitting the optical multiplexer M1 and the optical demultiplexer N1.

Also, lights from n optical fibers Fb may directly enter the photoelectric converters 51, 52, . . . , 5n by omitting the optical multiplexer M2 and the optical demultiplexer N2.

In the seventh embodiment (see FIG. 12), a case in which the AE wave detection system S7 includes a plurality of detection units (AE wave detectors 31, 32, . . . , n) has been described, but the present invention is not limited to such an example. That, is, the number of the above detection units may be one. Even in such a case, an AE wave can be detected based on change of optical power of light reflected by the optical filter 31f.

Also, each, embodiment may appropriately be combined. For example, the first embodiment (see FIG. 1) and the seventh embodiment (see FIG. 12) may be combined. In this case, light from the wideband light source 1 may be reflected/passed through by the optical filters 31f, 32f, . . . , 3nf (see FIG. 12) to extract change of the wavelength of light mutually reinforced by the FBG 31c, 32c, . . . , 3nc by n other optical filters 41, 42, . . . , 4n (not shown) as change of optical power.

In the above embodiments, a case in which the high-voltage apparatus G is a line has been described, but the present invention is not limited to such an example. The high-voltage apparatus G may be an electric apparatus, for example, an electrode converter, a generator, a motor, a transformer and the like. The high-voltage apparatus G may also be a power module.

Also in the above embodiments, a case in which an AE wave generated accompanying a partial discharge is detected as a sign of a dielectric breakdown has been described, but the present invention is not limited to such an example. Using the AE wave detector 3, for example, a deterioration diagnosis of iron bridges, railways, buildings and the like can be made and also a corrosion diagnosis of pipes and tanks can be made. Also using the AE wave detector 3, an abrasion diagnosis of bearings of a turbine can be made.

Each embodiment described above is described in detail to make the present invention easily understandable and is not necessarily limited to one including all described components. Also, a portion of the configuration of a certain embodiment may be replaced by the configuration of another embodiment. Also, the configuration of another embodiment may be added to the configuration of a certain embodiment. Also, addition, deletion, or substitution of another configuration may be made for a portion of the configuration of each embodiment.

A portion or all of each configuration, function processor, processing means and the like described above may be implemented by hardware, for example, by designing using an integrated circuit. In addition, mechanisms and configurations considered to be necessary to describe are shown and all mechanisms and configurations in terms of a product are not necessarily shown.

REFERENCE SIGNS LIST

S1, S2, S3, S4, S5, S6, S7 acoustic emission wave detection system
1 wideband light source
1A, 11A, 12A, . . . , 1nA laser diode
2, 21, 22, . . . , 2n optical circulator (optical guideway forming device)
3, 3A, 3B, 31, 32, . . . , 3n acoustic emission wave detector
3a, 31a, 32a, . . . , 3na optical fiber (first optical fiber)
3b, 31b, 32b, . . . , 3nb housing
3c, 31c, 32c, . . . , 3nc FBG (second optical fiber)
p upper end (one end)
q lower end (the other end)
r installation surface
3d optical connector
3f optical filter (first optical filter)
3g diffractive grating
3i mirror (mirror member)
31f, 32f, . . . , 3nf optical filter (second optical filter)
4, 41, 42, . . . , 4n optical filter (first optical filter)
5, 51, 52, . . . , 5n photoelectric converter
6, 61, 62, . . . , 6n amplifier (determination processor)
7, 71, 72, . . . , 7n AD converter (determination processor)
8 signal processor (determination processor)
11A, 12A, . . . , 1nA laser diode (light source)
G high-voltage apparatus

The invention claimed is:

1. An acoustic emission wave detector comprising:
a housing;
a first optical fiber that guides light from a light source into the housing; and
a second optical fiber housed inside the housing and having a diffractive grating that reflects the light guided into the housing, wherein
the second optical fiber is arranged in the housing so as to receive the light guided into the housing at one end of the second optical fiber and to receive an acoustic emission wave from an object at an opposite end of the second optical fiber, wherein the one end is spaced apart from the housing, and the opposite end is inserted into the housing through an insertion hole in the housing and fixed in the housing.

2. The acoustic emission wave detector according to claim 1, wherein
the second optical fiber is fixed in the housing such that the opposite end is directed to the object and the one end is directed in a direction opposite to the object when the acoustic emission wave is detected.

3. The acoustic emission wave detector according to claim 1, wherein
the housing has an installation surface on which the housing is installed on the object and
the second optical fiber is fixed in the housing such that an axis thereof is perpendicular to the installation surface.

4. The acoustic emission wave detector according to claim 1, further comprising:
an optical connector allowing the first optical fiber to be inserted into/removed from the housing.

5. The acoustic emission wave detector according to claim 1, further comprising:
a mirror member installed inside the housing, wherein
the mirror member is installed such that light entering the housing via the first optical fiber is reflected by the mirror member and reflected light propagates to the second optical fiber.

6. The acoustic emission wave detector according to claim 1, further comprising:
an optical filter installed inside the housing, wherein
the optical filter has characteristics to reflect light of a predetermined waveband included in light entering the housing via the first optical fiber and is installed such that reflected light propagates to the second optical fiber.

7. An acoustic emission wave detection system comprising:
an acoustic emission wave detector including a housing, a first optical fiber that guides light from a light source into the housing, and a second optical fiber having a diffractive grating that reflects the light guided into the housing and is arranged in the housing so as to receive the light guided into the housing at one end of the second optical fiber and to receive an acoustic emission wave from an object at an opposite end of the second optical fiber, wherein the one end is spaced apart from the housing, and the opposite end is inserted into the housing through an insertion hole in the housing and fixed in the housing;
a photoelectric converter that converts change of optical power of light originating from expansion and contraction of the second optical fiber and reflected by the diffractive grating into an electric signal; and
a determination processor that determines whether an acoustic emission wave has been generated in the object based on the electric signal input from the photoelectric converter.

8. The acoustic emission wave detection system according to claim 7, further comprising:
an optical filter that converts change of a wavelength of light reflected by the diffractive grating into the change of the optical power and outputs the change of the optical power to the photoelectric converter; and
an optical guideway forming device that allows light from the light source to the second optical fiber via the first optical fiber to propagate and also allows light to the optical filter via the first optical fiber after being reflected by the diffractive grating to propagate.

9. The acoustic emission wave detection system according to claim 7, further comprising:
an optical guideway forming device that allows light from the light source as a laser diode to the second optical fiber via the first optical fiber to propagate and also allows light to the photoelectric converter via the first optical fiber after being reflected by the diffractive grating to propagate, wherein
a wavelength of light of the laser diode is set such that the optical power of the light reflected by the diffractive grating changes due to expansion and contraction of the diffractive grating.

10. An acoustic emission wave detection system comprising:
a determination processor that determines whether an acoustic emission wave has been generated in an object based on an electric signal; and
a plurality of detection units, each of which includes:
an acoustic emission wave detector including a housing, a first optical fiber that guides light from a light source into the housing, and a second optical fiber having a diffractive grating that reflects the light guided into the housing and is arranged in the housing so as to receive the light guided into the housing at one end of the second optical fiber and to receive an acoustic emission wave from an object at an opposite end of the second optical fiber, wherein the one end is spaced apart from the housing, and the opposite end is inserted into the housing through an insertion hole in the housing and fixed in the housing; and a photoelectric converter that converts change of optical power of light originating from expansion and contraction of the second optical fiber and reflected by the diffractive grating into an electric signal;

wherein the determination processor determines whether the acoustic emission wave has been generated in the object based on the electric signal input from the photoelectric converter of each of the plurality of detection units.

11. The acoustic emission wave detection system according to claim 10, wherein each of the detection units includes:

an optical filter that converts change of a wavelength of light reflected by the diffractive grating into the change of the optical power and outputs the change of the optical power to the photoelectric converter; and an optical guideway forming device that allows light from the light source to the second optical fiber via the first optical fiber to propagate and also allows light to the optical filter via the first optical fiber after being reflected by the diffractive grating to propagate.

12. The acoustic emission wave detection system according to claim 10, wherein each of the detection units includes:

an optical guideway forming device that allows light from the light source as a laser diode to the second optical fiber via the first optical fiber to propagate and also allows light to the photoelectric converter via the first optical fiber after being reflected by the diffractive grating to propagate, wherein a wavelength of light of the laser diode corresponding to the diffractive grating is set such that the optical power of the light reflected by the diffractive grating changes due to expansion and contraction of the diffractive grating.

13. The acoustic emission wave detection system according to claim 10, wherein each of a plurality of the acoustic emission wave detectors has an optical filter that reflects light of a predetermined waveband included in light entering the housing via the first optical fiber and is installed such that reflected light propagates to the second optical fiber, the plurality of acoustic emission wave detectors is connected in series via the first optical fiber such that light having passed through the optical filter enters the housing of the other detection unit, further comprising:

an optical multiplexer that multiplexes lights emitted from a plurality of the light sources as laser diodes;

an optical demultiplexer that demultiplexes light joined in the first optical fiber after being reflected by the diffractive grating and is connected such that demultiplexed lights propagate to a plurality of the photoelectric converters; and an optical guideway forming device that allows light from the optical multiplexer to the second optical fiber via the first optical fiber to propagate and also allows light to the optical demultiplexer via the first optical fiber after being reflected by the diffractive grating to propagate, and a wavelength of light of the laser diode corresponding to the diffractive grating is set such that the optical power of the light reflected by the diffractive grating changes due to expansion and contraction of the diffractive grating.

14. An acoustic emission wave detection method comprising:

an optical power conversion step of extracting an acoustic emission wave generated in an object as change of optical power of light originating from expansion and contraction of a second optical fiber and reflected by a diffractive grating by an acoustic emission wave detector including a housing, a first optical fiber that guides light from a light source into the housing, and the second optical fiber having the diffractive grating that reflects the light guided into the housing and is arranged in the housing so as to receive the light guided into the housing at one end of the second optical fiber and to receive an acoustic emission wave from an object at an opposite end of the second optical fiber, wherein the one end is spaced apart from the housing, and the opposite end is inserted into the housing through an insertion hole in the housing and fixed in the housing;

a photoelectric conversion step of converting change of optical power extracted by the optical power conversion step into an electric signal; and a determination step of determining whether an acoustic emission wave has been generated in the object based on the electric signal input acquired by the photoelectric conversion step.

15. The acoustic emission wave detection method according to claim 14, wherein the object is an electric apparatus, a line, or a power module, and the determination processor determines an occurrence of an acoustic emission wave as a sign of a dielectric breakdown.

* * * * *